Figure 1:
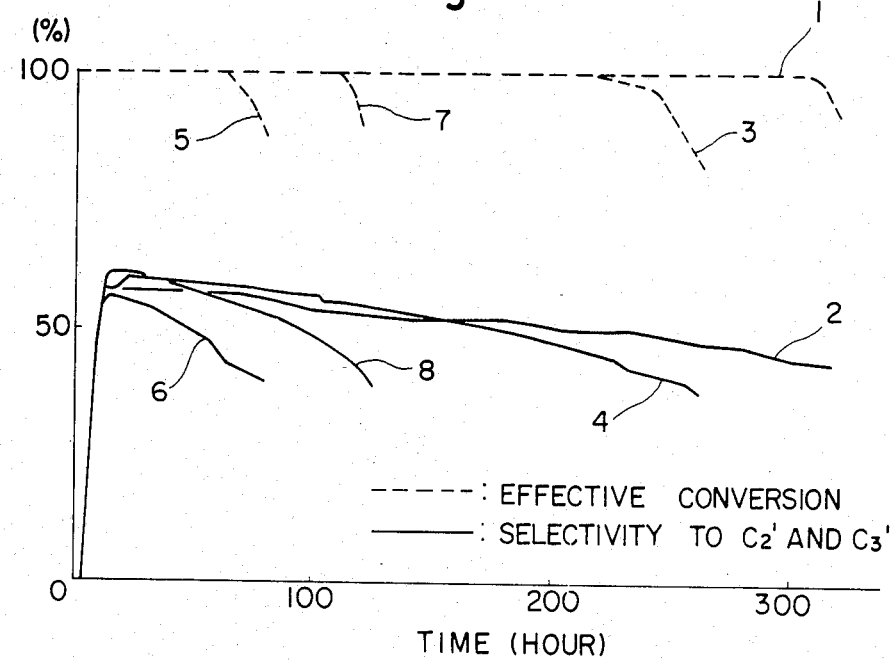

United States Patent [19]

Okado et al.

[11] Patent Number: 4,636,482

[45] Date of Patent: Jan. 13, 1987

[54] NOVEL ZEOLITE CATALYST AND METHOD OF PREPARING

[75] Inventors: Hideo Okado; Hiroshi Shoji, both of Ibaraki; Haruo Takaya, Abiko; Kichinari Kawamura, Tsuchiura; Yasuyoshi Yamazaki, Ibaraki, all of Japan

[73] Assignee: Director-General of Agency of Industrial Science & Technology, Tokyo, Japan

[21] Appl. No.: 735,981

[22] Filed: May 20, 1985

Related U.S. Application Data

[63] Continuation-in-part of Ser. No. 553,257, Nov. 18, 1983, Pat. No. 4,544,793.

[30] Foreign Application Priority Data

May 23, 1984 [JP] Japan ................................ 59-105530

[51] Int. Cl.$^4$ ............................................. B01J 29/06
[52] U.S. Cl. ........................................ 502/60; 502/77
[58] Field of Search ..................... 502/60, 77; 585/640

[56] References Cited

U.S. PATENT DOCUMENTS

| | | | |
|---|---|---|---|
| 3,702,886 | 11/1972 | Argauer et al. | 423/328 |
| 4,049,573 | 9/1977 | Kaeding | 585/640 X |
| 4,052,337 | 10/1977 | Nishikawa et al. | 502/60 |
| 4,066,714 | 1/1978 | Rodewald | 585/640 |
| 4,433,189 | 2/1984 | Young | 585/640 |
| 4,544,793 | 10/1985 | Okado et al. | 585/640 |

Primary Examiner—Carl F. Dees
Attorney, Agent, or Firm—Pahl, Lorusso & Loud

[57] ABSTRACT

A zeolite material obtained by modifying a crystalline aluminosilicate having the following empirical formula:

$$xM_2O.yM'O.Al_2O_3.zSiO_2.nH_2O$$

wherein M is an exchangeable cation selected from the group consisting of alkali metals, hydrogen and mixtures thereof, M' is an alkaline earth metal, x is between 0 and 1.5, y is between 0.2 and 40, z is between 50 and 3000 and n is between 0 and 40 and wherein x+y is at least 1.2, with an alkaline earth metal compound. The modifying may be by impregnation or by mere mixing. The zeolite material is useful as catalyst for converting methanol and/or dimethyl ether into lower olefins.

17 Claims, 2 Drawing Figures

NOVEL ZEOLITE CATALYST AND METHOD OF PREPARING

CROSS-REFERENCE TO RELATED APPLICATION

The present application is a continuation-in-part of U.S. Ser. No. 553,257, filed Nov. 18, 1983, and now issued as U.S. Pat. No. 4,544,793.

This invention relates to a novel synthetic aluminosilicate zeolite material and a method of preparing such a zeolite material. The present invention is also directed to a process for the production of lower olefins from methanol and/or dimethyl ether with the use of such a zeolite material as catalyst.

It is known that methanol and/or dimethyl ether can give hydrocarbons by catalytic conversion thereof. It is also known that zeolite materials are suited as catalyst for this purpose. Crystalline aluminosilicate zeolite materials, which are known as molecular sieves, are considered to be made up of an anionic three-dimensional framework of $SiO_4$ and $AlO_4$ cross-linked by the sharing of oxygen atoms, the anionic charge being balanced by the inclusion of the crystal of an exchangeable cation such as an alkali metal cation. Typical of such synthetic crystalline zeolites are "ZSM-5" and "ZSM-34" produced by Mobil Oil Corp. (See, for example, U.S. Pat. No. 3,702,886.) German Pat. No. 2,935,863 discloses a methanol conversion process using an H-ZSM-5 (proton-type ZSM-5) catalyst. This process gives lower olefins with a maximum yield of 70.1 wt % at a reaction temperature of about 550° C., the yield being lowered as the reaction temperature is lowered. At a temperature of 550° C. or more, the catalyst deteriorates within relatively a short period of time due to the deposition of coke on the surface of the catalyst.

In U.S. patent application Ser. No. 553,257 assigned to Director-General of Agency of Industrial Science and Technology, there is disclosed a process for the production of olefins by catalytic conversion of methanol and/or dimethyl ether, using a high alkaline earth metal-content synthetic zeolite catalyst. With such a catalyst, the yield of benzene, toluene and xylene, which are precursor materials for coke, is reduced so that the service life of the catalyst is much longer as compared with the conventional zeolite catalysts such as ZSM-5.

The present invention pertains to an improvement in the catalyst disclosed in the above U.S. patent application. In accordance with the present invention there is provided a zeolite material obtained by modifying a crystalline aluminosilicate having the following empirical formula:

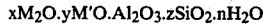

$xM_2O.yM'O.Al_2O_3.zSiO_2.nH_2O$ wherein M is an exchangeable cation selected from the group consisting of alkali metals, hydrogen and mixtures thereof, M' is an alkaline earth metal, x is between 0 and 1.5, y is between 0.2 and 40, z is between 50 and 3000 and n is between 0 and 40 and wherein x+y is at least 1.2, with an alkaline earth metal compound. The zeolite material of the present invention has significantly improved service life as compared with the high alkaline earth metal-content zeolite disclosed in the above-described U.S. application or ZSM-5 modified with an alkaline earth metal compound.

The zeolite material of the present invention may be prepared using the crystalline aluminosilicate of the above-described U.S. patent application Ser. No. 553,257 the disclosure of which is hereby incorporated by reference. Briefly, the crystalline aluminosilicate may be prepared by hydrothermally treating a mixture containing water, a tetrapropylammonium compound and a source of an alkali metal oxide, an oxide of silicon, an oxide of aluminum and an oxide of an alkaline earth metal. The mixture has the following composition: a $SiO_2/Al_2O_3$ molar ratio of 12–3000, preferably 50–500; a $OH^-/SiO_2$ molar ratio of 0.02–10, preferably 0.1–0.5; a $H_2O/SiO_2$ molar ratio of 1–1000, preferably 30–80; a tetrapropylammonium ion/$SiO_2$ molar ratio of 0.02–2, preferably 0.05–0.5; and an alkaline earth metal/Al atomic ratio of 0.03–300, preferably 0.5–8.

The mixture is subjected to a hydrothermal treatment to form crystals of the aluminosilicate. Preferably, the mixture is maintained at a temperature of 80°–200° C., more preferably 150°–180° C., for 1–200 hours, preferably 5–50 hours, under pressure or normal pressure with stirring. The reaction produce in the form of crystals is separated by filtration or centrifuge, washed with water for the removal of unassociated ions and dried. The dried aluminosilicate as such may be used as starting material for the production of the zeolite material of this invention. Alternately, the dried aluminosilicate may be calcined at about 520° C. before being modified with the alkaline earth metal compound. The aluminosilicate which has been converted into a proton form may also be suitably used as a raw material.

The modification of the crystalline aluminosilicate may be effected by impregnation or mere mixing with an alkaline earth metal compound. The alkaline earth metal compound used for the modification of the aluminosilicate may be, for example, a salt, an oxide or a hydroxide of an alkaline earth metal. Examples of suitable alkaline earth metal compounds include carboxylic acid salts such as acetates of alkaline earth metals, inorganic acid salts such as carbonates, nitrates, phosphates and borates of alkaline earth metals. Carboxylates such as acetates of Ca, Sr and Ba give carbonates when heated in the air at 500°–600° C.

In the case of the modification by impregnation, the aluminosilicate is immersed in a solution containing an alkaline earth metal compound to impregnate the aluminosilicate with the alkaline earth metal compound. The mixture is then heated for the evaporation of the solvent, generally water, till dryness. Alternately, the aluminosilicate immersed in the solution is separated therefrom by filtration or centrifuge and dried. In either case, the dried aluminosilicate may be calcined at a temperature of 500°–600° C. in the air or in a nitrogen atmosphere.

In the case of the modification by mixing, the aluminosilicate is used in the form of a fine particulate with a particle size of 30 μm or less, preferably 20 μm or less, most preferably 10 μm or less. The coexistence of 30 μm or coarser particles does not adversely affect the catalytic properties, however. The alkaline earth metal compound to be mixed with the aluninosilicate is also in the form of a fine particulate with a particle size of 20 μm or less, preferably 10 μm or less, most preferably 5 μm or less. The presence of alkaline earth metal compound particles of 20 μm or more does not adversely affect the catalytic properties, however. Mixing may be effected by, for example, pulverizing the alkaline earth metal compound and the aluminosilicate together.

If desired, the mixing of the aluminosilicate and alkaline earth metal compound may be performed in the presence of a suitable liquid medium which is a poor solvent for the alkaline earth metal compound, such as water in the case of carbonates and hydroxides. Thus, the aluminosilicate and alkaline earth metal compound may be formed into a slurry or paste for mixing.

The aluminosilicate thus mixed with the alkaline earth metal compound may be used as such or after calcination in the air or a nitrogen atmosphere, generally at a temperature of 500°-600° C. for the conversion of methanol into olefins.

The amount of the alkaline earth metal compound incorporated into the aluminosilicate for modification thereof is generally at least 0.25 %, in terms of elemental metal, preferably 1-35 wt %, based on the weight of the unmodified aluminosilicate. More preferably, the amount is 5-20 wt % in the case of magnesium, calcium or strontium compounds, and 5-35 wt % in the case of barium compounds.

The zeolite material of the present invention is generally used in the proton form for the production of olefins from methanol. The proton-type zeolite material may be obtained by using a proton-type crystalline aluminosilicate as a raw material to be modified with the alkaline earth metal compound. The proton-type crystalline aluminosilicate in turn may be prepared by ion exchanging the alkali metal ion M thereof with proton. The ion exchange with proton may be performed in any known manner. For example, the aluminosilicate is treated with an aqueous solution of an ammonium compound such as ammonium chloride so that the alkali metal ion may be ion exchanged with ammonium ion. The resulting product is then washed, dried and calcined for the elimination of ammonia. Alternately, the ion exchange may be effected by treatment with hydrochloric acid, followed by washing, drying and calcination. In either case, the calcination is generally performed at a temperature of 300°-700° C. for 1-100 hours. Through the above ion exchange treatment, a part of the alkaline earth metal M' of the aluminosilicate is also ion exchanged with proton. Since the ammonium-type aluminosilicate may be converted into proton-type by mere calcination thereof, it is advantageous to first modify the ammonium-type aluminosilicate with the alkaline earth metal compound prior to conduct the calcination.

The production of olefins from methanol and/or dimethyl ether according to the process of the present invention may be conducted by contacting a gas stream containing methanol and/or dimethyl ether with the zeolite catalyst at a temperature of 300°-650° C., preferably 350°-600° C., a pressure of 0.1-100 atm, preferably 0.5-10 atm with a liquid hourly space velocity of 0.1-20 $Hr^{-1}$. The gas stream may also contain steam, nitrogen, argon or the like inert gas. The reaction can be effected in any suitable system such as a fixed bed, a fluidized bed or a moving bed system. The zeolite material may be used either by itself or, if desired, in combination with other substances such as clay, kaolin and alumina.

Because of the excellent catalytic properties of the zeolite material, the process of the present invention can yield lower olefins with a high selectivity and a high yield while minimizing the production of CO, $CO_2$, paraffinic hydrocarbons and aromatic hydrocarbons. In addition, the process can be continued for a long period of time without encountering the problem of coke deposition and resulting reduction of catalytic activities.

The following examples and the accompanying drawings will further illustrate the present invention.

Figure 2:
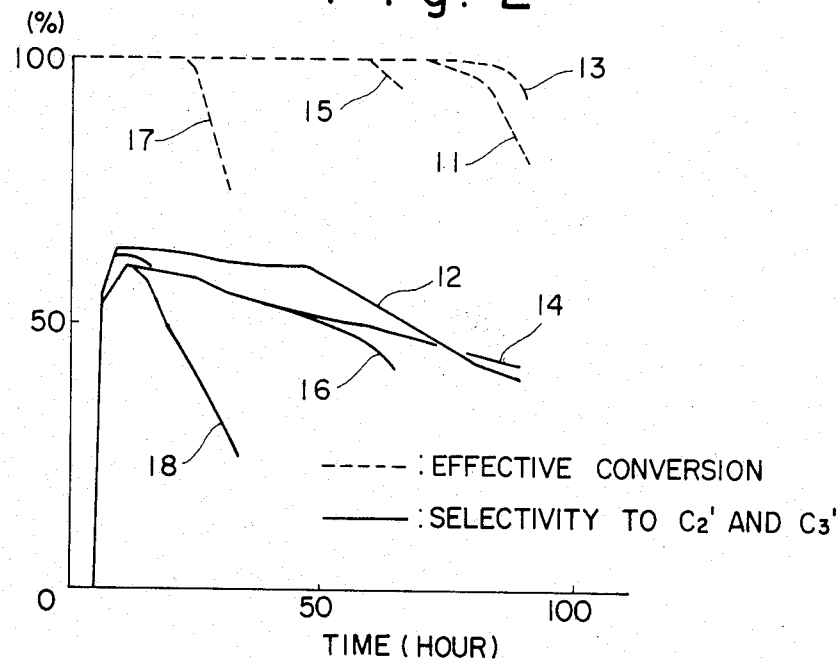

In the drawings:

FIG. 1 is a graph showing the results obtained in Examples 5 and 6 and Comparative Examples 3 and 4 and indicating the change in effective conversion (dotted lines) and in selectivity to ethylene and propylene (solid lines) of each of the zeolite catalysts of Examples 1 and 2 and Comparative Examples 1 and 2; and FIG. 2 is a graph, similar to FIG. 1, showing the results obtained in Examples 7-10 and Comparative Example 5.

PREPARATION OF ZEOLITE CATALYSTS

Comparative Example 1

1.14 Grams of aluminum nitrate nonahydrate were dissolved in 90 g of water, with which were mixed, with vigorous stirring, 100 g of a water glass solution containing 60 g of a water glass (Cataloid SI-30, made by Shokubai Kasei K.K. and containing 30.5% of $SiO_2$ and 0.42% of $Na_2O$) and 40 g of water. Thereafter, the resulting mixture was mixed with 21.26 g of a solution consisting of 1.26 g of sodium hydroxide and 20 g of water and then with 38.11 g of a solution consisting of 8.11 g of tetrapropylammonium bromide and 30 g of water to obtain a gel with a molar ratio of $SiO_2$ to $Al_2O_3$ of 200.

The gel was then charged in a 300 ml autoclave and subjected to a hydrothermal treatment at a temperature of 160° C. for 18 hours with stirring. The resulting product was then separated, by means of a centrifugal device, into a liquid phase and a solid phase. The solid phase was washed well with water and dried at 120° C. for 5 hours, followed by calcination at 520° C. for 10 hours. The calcined product was mixed with 0.6N hydrochloric acid (15 ml per 1 g of the calcined product) and stirred at room temperature for 24 hours. After filtration, the solid phase was washed well with water, dried at 120° C. and calcined in the air at 520° C. for 5 hours to obtain an H-ZSM-5 catalyst (Si: 43.1 wt %, Al:0.45 wt %). The H-ZSM-5 ($SiO_2/Al_2O_3$: 200) thus obtained (5 g) was mixed with 13.14 g of a solution consisting of 3.14 g of calcium acetate monohydrate and 10 g of water, and the resulting mixture was stirred at about 80° C. for 20 hours. The mixture was poured into an evaporating dish and heated at 100°-110° C. for the evaporation of water. The resulting dried residue was calcined at 200° C. for 2 hours and 500° C. for 18 hours to obtain a Ca-modified ZSM-5 catalyst containing 0.144 g of Ca per 1 g of the zeolite.

Comparative Example 2

1.14 Grams of aluminum nitrate nonahydrate and 1.34 g of calcium acetate monohydrate were dissolved in 90 g of water, with which were mixed, with vogorous stirring, 100 g of a water glass solution containing 60 g of a water glass (Cataloid SI-30, made by Shokubai Kasei K.K. and containing 30.5% of $SiO_2$ and 0.42% of $Na_2O$) and 40 g of water. Thereafter, the resulting mixture was mixed with 21.26 g of a solution consisting of 1.26 g of sodium hydroxide and 20 g of water and then with 38.11 g of a solution consisting of 8.11 g of tetrapropylammonium bromide and 30 g of water to obtain a gel with a molar ratio of $SiO_2$ to $Al_2O_3$ of 200.

The gel was then charged in a 300 ml autoclave and subjected to a hydrothermal treatment at a temperature of 160° C. for 18 hours with stirring. The resulting product was then separated, by means of a centrifugal device, into a liquid phase and a solid phase. The solid phase was washed well with water and dried at 120° C. for 5 hours, followed by calcination at 520° C. for 10 hours. Subsequently, the calcined product was immersed in 0.6N hydrochloric acid (15 ml per 1 g of the calcined product) and the mixture was stirred at room temperature for 24 hours. After filtration, the solid phase was washed well with water, dried at 120° C. and calcined in the air at 520° C. for 10 hours to obtain a Ca-containing, proton-type zeolite catalyst (Si: 43.2 wt %, Al: 0.44 wt %, Ca: 0.70 wt %).

Example 1

The Ca-containing zeolite (5 g) obtained in Comparative Example 2 above was mixed with 13.14 g of an aqueous solution containing 3.14 g of calcium acetate monohydrate and the mixture was stirred at about 80° C. for 20 hours. The resulting mixture was then heated at 100°-110° C. to evaporate its water. The dried mass was then calcined in the air at 200° C. for 2 hours and then at 500° C. for 18 hours to obtain a Ca-modified, Ca-containing zeolite catalyst (Ca: 12.7 wt %). The electron micrograph of the thus obtained catalyst showed that the zeolite was mainly composed of particles with 2-7 μm and that the calcium component incorporated by the above-described modification treatment was in the form of fine particulates mainly having a particle size of 1 μm or less and evenly dispersed in and deposited on the zeolite particles.

Example 2

The Ca-containing zeolite (5 g) obtained in Comparative Example 2 was mixed with 15 g of an aqueous solution containing 5 g of strontium nitrate and the mixture was maintained at about 80° C. with stirring for 2 hours, followed by centrifugation for the separation of the Sr-impregnated zeolite. The zeolite thus separated was dried at 90° C. for 10 hours and calcined at 500° C. for 3 hours to obtain a Sr-modified, Ca-containing zeolite catalyst (Ca: 0.50 wt %, Sr: 7.1 wt %). The catalyst gave an electron micrograph similar to that of the Ca-modified, Ca-containing zeolite catalyst obtained in Example 1 above.

Example 3

Calcium acetate was calcined at 500° C. and finely ground in a mortar to obtain ground calcium carbonate. The Ca-containing zeolite (5 g) obtained in Comparative Example 2 was commingled with 1.8 g of the ground calcium carbonate to obtain Ca-modified, Ca-containing zeolite catalyst (Ca: 11.1 wt %). The electron micrograph of the thus obtained catalyst revealed that the catalyst contained a larger amount of large particles than the catalyst obtained in Example 1 above and that the distribution of the calcium particles having a particle size of 1 μm or less in the zeolite particles was less homogeneous than that of the catalyst obtained in Example 1 above.

Example 4

The Ca-containing zeolite (5 g) obtained in Comparative Example 2 was commingled in a mortar with 1.8 g of finely divided, commercially available calcium carbonate to obtain a Ca-modified, Ca-containing zeolite catalyst (Ca: 11.1 wt %). The electron micrograph of the thus obtained catalyst showed that the distribution of the calcium particles was almost the same as that of the calcium of the catalyst of Example 3 above. However, the calcium particles were rigid and rugged unlike those of the catalysts of Examples 1 and 3 which were soft and porous.

PRODUCTION OF OLEFINS FROM METHANOL

Example 5

The Ca-modified, Ca-containing zeolite catalyst obtained in Example 1 was shaped into tablets by compression at 400 Kg/cm$^2$ and the resultant tablets were ground into particles. The ground catalyst (2 ml) with a size in the range of 10-20 mesh (Tyler) was packed in a tubular reactor with an inside diameter of 10 mm. Liquid methanol was continuously fed to a vaporizer at a rate of 4 ml/hr and the methanol gas was introduced, at normal pressure, into the reactor together with argon gas supplied at a rate of 40 ml/min. Thus, the reaction was performed with a liquid hourly space velocity (LHSV) of 2 Hr$^{-1}$. The reaction temperature was 550° C. The gas discharged from the reactor was occasionally sampled to analyze the composition thereof by gas chromatography. The results are shown in Table 1 and by way of a graph in FIG. 1 (curves 1 and 2). In Table 1, the term "Effective Conversion" means a conversion calculated in terms of carbon in which dimethyl ether is regarded as being unreacted starting material.

$$\text{Effective Conversion} = 100 - \frac{\text{Amount of methanol and dimethyl ether}}{\text{Amount of Starting methanol}} \times 100$$

The term "Selectivity" is intended to mean a selectivity calculated in terms of carbon in which dimethyl ether is regarded as being unreacted starting material.

$$\text{Selectivity} = \frac{\text{Yield of the material concerned}}{\text{Effective conversion}} \times 100$$

Example 6

Example 5 was repeated in the same manner as described using the Sr-modified, Ca-containing zeolite catalyst obtained in Example 2 above. The results were as shown in Table 1 and in FIG. 1 (curves 3 and 4).

TABLE 1

| | Example 5 | | | | Example 6 | | | |
|---|---|---|---|---|---|---|---|---|
| Catalyst | Example 1 | | | | Example 2 | | | |
| Reaction Temperature (°C.) | 550 | 550 | 550 | 550 | 550 | 550 | 550 | 550 |
| Reaction Time (hr)*1 | 5 | 100 | 285 | 310 | 5 | 100 | 210 | 250 |
| Methanol Conversion (%) | 99.60 | 99.67 | 100.00 | 97.25 | 99.52 | 99.41 | 99.43 | 91.16 |
| Effective Conversion (%) | 99.60 | 99.67 | 100.00 | 93.68 | 99.52 | 99.41 | 99.40 | 81.55 |

TABLE 1-continued

| | Example 5 | | | | Example 6 | | | |
|---|---|---|---|---|---|---|---|---|
| Selectivity (%) | | | | | | | | |
| CO | 0.36 | 0.25 | 0.72 | 0.60 | 0.62 | 0.49 | 0.40 | 0.75 |
| $CO_2$ | 0.71 | 0.47 | 0.73 | 0.63 | 0.64 | 0.52 | 0.47 | 0.56 |
| $CH_4$ | 0.49 | 0.35 | 0.83 | 0.99 | 0.51 | 0.36 | 1.90 | 1.98 |
| $C_2H_4$ | 12.05 | 9.06 | 6.55 | 5.47 | 9.68 | 7.30 | 5.30 | 4.11 |
| $C_2H_6$ | 0.00 | 0.00 | 0.00 | 0.00 | 0.00 | 0.00 | 0.00 | 0.11 |
| $C_3H_6$ | 48.22 | 45.77 | 39.36 | 37.71 | 47.38 | 46.21 | 41.18 | 30.94 |
| $C_3H_8$ | 0.61 | 0.50 | 0.35 | 0.29 | 0.42 | 0.34 | 0.25 | 0.18 |
| $C_4H_8$ | 17.96 | 17.59 | 15.44 | 15.16 | 17.62 | 17.54 | 16.04 | 13.76 |
| $i-C_4$ | 0.66 | 0.63 | 0.46 | 0.44 | 0.50 | 0.50 | 0.43 | 0.33 |
| $n-C_4$ | 0.24 | 0.22 | 0.18 | 0.15 | 0.18 | 0.17 | 0.13 | 0.10 |
| $C_5H_{10}$ | 6.58 | 10.81 | 12.30 | 13.15 | 6.88 | 10.97 | 13.04 | 12.95 |
| $C_5H_{12}$ | 5.05 | 5.14 | 4.69 | 4.77 | 4.79 | 4.89 | 4.95 | 4.67 |
| Ethanol | 0.00 | 0.00 | 0.00 | 0.00 | 0.21 | 0.27 | 0.66 | 0.00 |
| Benzene | 0.26 | 0.20 | 0.74 | 0.17 | 0.17 | 0.21 | 0.24 | 0.31 |
| Toluene | 0.32 | 0.25 | 0.83 | 0.14 | 0.38 | 0.25 | 0.19 | 0.19 |
| Xylene | 0.19 | 0.25 | 0.31 | 0.28 | 0.27 | 0.25 | 0.40 | 0.69 |
| uKHC*2 | 6.28 | 8.50 | 16.52 | 20.04 | 9.73 | 9.73 | 14.43 | 28.37 |
| Total | 99.98 | 99.99 | 100.01 | 99.99 | 99.98 | 100.00 | 100.01 | 100.00 |
| $C_2' + C_3'$*3 | 60.27 | 54.83 | 45.91 | 43.18 | 57.06 | 53.51 | 46.48 | 35.05 |

*1 Measurement was commenced after the reaction temperature became 550° C.
*2 Other hydrocarbons
*3 Selectivity to ethylene and propylene Comparative Example 3

Example 5 was repeated in the same manner as described using the Ca-modified ZSM-5 catalyst obtained in Comparative Example 1 above. The results are shown in Table 2 and FIG. 1 (curves 5 and 6).

Comparative Example 4

Example 5 was repeated in the same manner as described using Ca-containing zeolite catalyst obtained in Comparative Example 2 above. The results are shown in Table 2 and FIG. 1 (curves 7 and 8).

TABLE 2

| | Comparative Example 3 | | | | Comparative Example 4 | | |
|---|---|---|---|---|---|---|---|
| Catalyst | Comparative Example 1 | | | | Comparative Example 2 | | |
| Reaction Temperature (°C.) | 550 | 550 | 550 | 550 | 550 | 550 | |
| Reaction Time (hr)*1 | 2 | 52 | 68 | 5 | 100 | 115 | |
| Methanol Conversion (%) | 100.00 | 99.47 | 94.84 | 99.39 | 99.11 | 94.97 | |
| Effective Conversion (%) | 100.00 | 98.99 | 90.25 | 99.39 | 99.11 | 89.83 | |
| Selectivity (%) | | | | | | | |
| CO | 3.05 | 1.58 | 2.20 | 0.00 | 0.47 | 0.61 | |
| $CO_2$ | 2.16 | 1.77 | 1.92 | 0.00 | 0.04 | 0.00 | |
| $CH_4$ | 2.03 | 2.43 | 3.04 | 0.52 | 3.61 | 4.67 | |
| $C_2H_4$ | 9.46 | 5.41 | 4.19 | 14.55 | 8.62 | 7.21 | |
| $C_2H_6$ | 0.26 | 0.17 | 0.15 | 0.00 | 0.03 | 0.26 | |
| $C_3H_6$ | 45.68 | 40.74 | 35.71 | 46.92 | 37.75 | 30.83 | |
| $C_3H_8$ | 1.00 | 0.49 | 0.41 | 0.81 | 0.39 | 0.32 | |
| $C_4H_8$ | 18.28 | 16.41 | 15.61 | 17.18 | 13.97 | 12.24 | |
| $i-C_4$ | 0.70 | 0.63 | 0.60 | 0.69 | 0.42 | 0.33 | |
| $n-C_4$ | 0.39 | 0.21 | 0.20 | 0.29 | 0.15 | 0.14 | |
| $C_5H_{10}$ | 6.79 | 12.80 | 13.26 | 5.09 | 9.78 | 10.12 | |

TABLE 2-continued

| | Comparative Example 3 | | | Comparative Example 4 | | |
|---|---|---|---|---|---|---|
| $C_5H_{12}$ | 4.74 | 4.70 | 4.81 | 4.80 | 4.25 | 4.06 |
| Ethanol | 0.18 | 0.39 | 0.00 | 0.37 | 0.63 | 0.24 |
| Benzene | 0.25 | 0.19 | 0.22 | 0.38 | 0.46 | 0.63 |
| Toluene | 0.65 | 0.24 | 0.14 | 1.17 | 1.06 | 0.84 |
| Xylene | 0.87 | 0.55 | 0.48 | 1.39 | 3.08 | 3.75 |
| uKHC*2 | 3.32 | 11.28 | 17.04 | 5.86 | 14.29 | 23.76 |
| Total | 100.01 | 99.99 | 99.98 | 100.02 | 99.99 | 100.00 |
| $C_2' + C_3'$*3 | 55.14 | 46.15 | 39.90 | 61.47 | 46.37 | 38.04 |

Examples 7–10

Using the catalysts obtained in Examples 1–4 above, methanol conversion was effected in the same manner as described in Example 5 above except that the amount of the catalyst packed in the reactor was 1 ml (i.e. LHSV=4 $Hr^{-1}$) and the reaction was performed at 600° C. By increasing the reaction temperature from 550° C. to 600° C., the service life of the zeolite catalysts is reduced to about half. Further, by making LHSV double, the service life is also reduced to half. Therefore, the reaction conditions of the Examples 7–10 are regarded as being 4 times as severe as those of Example 5 above. The results are shown in Table 3 and by way of a graph in FIG. 2. In FIG. 2, the curves 11 and 12 show the results of Examples 7 and 9 obtained with the catalysts of Examples 1 and 3, the curves 13 and 14 show the results of Example 8 obtained with the catalyst of Example 2, and the curves 15 and 16 show the results of Example 10 obtained with the catalyst of Example 4.

Comparative Example 5

Example 7 was repeated in the same manner as described except that the catalyst used was Ca-containing zeolite obtained in Comparative Example 2. The results are shown in Table 3 and FIG. 2 (curves 17 and 18).

TABLE 3

| | Catalyst | Reaction temperature (°C.) | Reaction time (hr) | Methanol conversion (%) | Effective conversion (%) | Selectivity (%) | | | |
|---|---|---|---|---|---|---|---|---|---|
| | | | | | | $C_2'$ | $C_3'$ | $C_2' + C_3'$ | B.T.X. |
| Example 7 | Example 1 | 600 | 5 | 99.72 | 99.72 | 14.96 | 49.52 | 64.48 | 0.51 |
| | " | | 66 | 98.10 | 98.10 | 7.57 | 37.33 | 44.90 | 0.54 |
| | " | | 80 | 91.19 | 84.20 | 6.46 | 33.50 | 39.96 | 0.59 |

TABLE 3-continued

| | Catalyst | Reaction temperature (°C.) | Reaction time (hr) | Methanol conversion (%) | Effective conversion (%) | Selectivity (%) | | | |
|---|---|---|---|---|---|---|---|---|---|
| | | | | | | $C_2'$ | $C_3'$ | $C_2' + C_3'$ | B.T.X. |
| Example 8 | Example 2 | 600 | 5 | 99.57 | 99.57 | 12.22 | 48.36 | 60.58 | 0.86 |
| | " | | 68 | 99.34 | 99.34 | 7.93 | 38.82 | 46.75 | 0.45 |
| | " | | 80 | 97.84 | 97.84 | 6.69 | 36.23 | 42.92 | 0.42 |
| Example 9 | Example 3 | 600 | 5 | 99.70 | 99.70 | 15.24 | 48.78 | 64.02 | 0.53 |
| | " | | 67 | 98.53 | 98.53 | 8.11 | 38.54 | 46.65 | 0.55 |
| | " | | 80 | 91.42 | 84.78 | 6.89 | 33.91 | 40.80 | 0.57 |
| Example 10 | Example 4 | 600 | 5 | 99.58 | 99.58 | 15.24 | 46.91 | 62.15 | 0.69 |
| | " | | 50 | 98.08 | 98.08 | 10.01 | 35.25 | 45.26 | 1.05 |
| | " | | 60 | 93.88 | 93.88 | 9.35 | 31.47 | 40.82 | 1.22 |
| Comparative Example 5 | Comparative Example 2 | 600 | 5 | 99.32 | 99.32 | 17.01 | 45.10 | 62.11 | 5.02 |
| | | " | 17 | 98.07 | 98.07 | 10.03 | 31.24 | 41.27 | 7.14 |
| | | " | 25 | 83.30 | 56.84 | 6.25 | 19.40 | 25.65 | 4.97 |

We claim:

1. A zeolite material obtained by modifying a crystalline aluminosilicate, said aluminosilicate having the following empirical formula:

$$xM_2O.yM'O.Al_2O_3.zSiO_2.nH_2O$$

wherein M is an exchangeable cation selected from the group consisting of alkali metals, hydrogen and mixtures thereof, M' is an alkaline earth metal selected from the group consisting of calcium, strontium and barium, x is between 0 and 1.5, y is between 1.2 and 40, z is between 70 and 3000 and n is between 0 and 40 and wherein x+y is at least 1.2, said modifying being by incorporation of a calcium, strontium or barium compound.

2. A zeolite material as claimed in claim 1, wherein said modifying is by impregnating the crystalline aluminosilicate with a solution containing the alkaline earth metal compound, followed by drying.

3. A zeolite material as claimed in claim 2, wherein y is between 1.4 and 40 and z is between 97.7 and 3000.

4. A zeolite material as claimed in claim 1, wherein said modifying is by commingling the crystalline aluminosilicate with fine particulates of the alkaline earth metal compound.

5. A zeolite material as claimed, in claim 4, wherein y is between 1.2 and 40 and z is between 70 and 3000.

6. A zeolite material as claimed in claim 4, wherein the crystalline aluminosilicate and the alkaline earth metal compound have particle sizes of 30 μm or less and 20 μm or less, respectively.

7. A zeolite material as claimed in claim 4, wherein the content of the alkaline earth metal compound is at least 0.25 wt %, in terms of elemental metal, based on the weight of the crystalline aluminosilicate.

8. A zeolite material as claimed in claim 4, wherein the alkaline earth metal compound is a strontium compound or a calcium compound.

9. A zeolite material as claimed in claim 8, wherein the alkaline earth metal compound includes strontium carbonate or calcium carbonate.

10. A zeolite material as claimed in claim 1, wherein M' is Ca or Sr.

11. A method of preparing a zeolite material, comprising the steps of:
providing a crystalline aluminosilicate having the following empirical formula:

$$xM_2O.yM'O.Al_2O_3.zSiO_2.nH_2O$$

wherein M is an exchangeable cation selected from the group consisting of alkali metals, hydrogen and mixtures thereof, M' is an alkaline earth metal, x is between 0 and 1.5, y is between 0.2 and 40, z is between 50 and 3000 and n is between 0 and 40 and wherein x+y is at least 1.2; and
modifying the crystalline aluminosilicate by commingling the crystalline aluminosilicate with fine particulates of an alkaline earth metal compound.

12. A method as claimed in claim 11, wherein the alkaline earth metal compound is strontium carbonate or calcium carbonate.

13. A method as claimed in claim 11, wherein the crystalline aluminosilicate and the alkaline earth metal compound have particle sizes of 30 μm or less and 20 μm or less, respectively.

14. A method of preparing a zeolite material, comprising the steps of:
providing a crystalline aluminosilicate having the following empirical formula:

$$xM_2O.yM'O.Al_2O_3.zSiO_2.nH_2O$$

wherein M is an exchangeable cation selected from the group consisting of alkali metals, hydrogen and mixtures thereof, M' is an alkaline earth metal selected from the group consisting of calcium, strontium and barium, x is between 0 and 1.5, y is between 1.2 and 40, z is between 70 and 3000 and n is between 0 and 40 and wherein x+y is at least 1.2; and
modifying the crystalline aluminosilicate by impregnating the crystalline aluminosilicate with a solution containing a compound of an alkaline earth metal selected from the group consisting of calcium, strontium and barium.

15. A method as claimed in claim 14, wherein the alkaline earth metal compound is strontium carbonate or calcium carbonate.

16. A method as claimed in claim 14, wherein the crystalline aluminosilicate and the alkaline earth metal compound have particle sizes of 30 μm or less and 20 μm or less respectively.

17. The zeolite material of claim 4 wherein said modifying calcium, strontium or barium compound is present in said zeolite material in the amount of 5-20% by weight, based on the weight of said aluminosilicate.

* * * * *